United States Patent [19]

Mercer

[11] 4,346,095
[45] Aug. 24, 1982

[54] THERAPEUTIC TREATMENT FOR VIRAL HEPATITIS INFECTION

[76] Inventor: James B. Mercer, 13109 W. 95th St., Lenexa, Kans. 66215

[21] Appl. No.: 64,072

[22] Filed: Aug. 6, 1979

Related U.S. Application Data

[63] Continuation-in-part of Ser. No. 876,618, Feb. 10, 1978, Pat. No. 4,177,281.

[51] Int. Cl.$^3$ ............................................. A61K 31/415
[52] U.S. Cl. ................................................. 424/273 R
[58] Field of Search ..................................... 424/273 R

[56] References Cited
U.S. PATENT DOCUMENTS 3,442,899  5/1969  Mercer ................................. 424/273

OTHER PUBLICATIONS

Taylor, Metronidazole—A New Agent for Combined Somatic and Physic Therapy of Alcoholism, (Date Unknown).

Primary Examiner—Jerome D. Goldberg
Attorney, Agent, or Firm—Fishburn, Gold & Litman

[57] ABSTRACT

The administration internally to humans of 1-(B-hydroxethyl)-2-methyl-5-nitromidazole, (metronidazole) in a dosage range for adult humans of about 31 to 2,500 mgs per twenty-four hour period, is an effective therapeutic treatment for certain viral infections causing diverse symptoms both acute and chronic. Corresponding dosage proportional to body weight appears effective in other mammals also.

4 Claims, No Drawings

THERAPEUTIC TREATMENT FOR VIRAL HEPATITIS INFECTION

This is a Continuation-in-Part of application Ser. No. 876,618 filed Feb. 10, 1978, entitled THERAPEUTIC TREATMENT FOR VIRAL INFECTION, now U.S. Pat. No. 4,177,281. Reference is also made to related U.S. Pat. Nos. 4,073,928; 3,752,889; 3,856,966 and 3,952,103.

The invention herein described related to a method of treating certain viral infections in humans such as regional ileitis (Crohn's disease), viral thyroiditis, multiple-sclerosis, viral hepatitis, carpal tunnel syndrome, psoriasis, amyotrophic lateral sclerosis, cytomegalovirus infection, viral bilateral macular degeneration of the retina, sarcoidosis, viral diverticulitis and measles (Rubeola). The treatment also appears effective in the extension of life span which may result from the inhibition of such continuing viral disease. In other mammals, viral diseases such as distemper and scrapie in sheep apparently respond to the treatment. It is noted that multiple sclerosis in humans has been linked to canine distemper virus in humans.

The objects of this invention are: to provide a method for systematically treating certain viral infections in humans; to provide such a treatment which is effective in combating viral infections in humans such as regional ileitis (Crohn's disease), viral thyroiditis, multiple-sclerosis, viral hepatitis, carpal tunnel syndrome, psoriasis, amyotrophic lateral sclerosis, cytomegalovirus infection, viral bilateral macular degeneration of the retina, measles and corresponding diseases in other mammals such as distemper and scrapie in sheep; to provide such a method which appears effective in the extension of life span which may result from the inhibition of continuing viral disease; to provide such a method that is suitable for intensive therapy as well as long-term maintenance and intermittent therapy; and to provide such a treatment which is easily administered and usually well tolerated by the recipient.

1-(B-hydroxyethyl)-2-methyl-5-nitromidazole, (metronidazole) is a known alkylating agent of relatively low toxicity in mammals which is thought to interfere with nucleic acid biosynthesis. It appears that metronidazole can penetrate all tissues of the body quite readily and its effectiveness, in the treatment of viral infections, is believed to relate to blockage or interference with the viral metabolism cycle necessary for cell infection. The agent apparently suppresses viral production while natural body defenses function to eliminate viral material from the system. Metronidazole is readily absorbable from the human intestinal tract and may be administered orally as well as by vaginal or rectal inserts, as indicated.

Clinical observations upon the administration of metronidazole have demonstrated marked patient improvement and in many cases, apparent complete remissions in statistically significant numbers of patients diagnosed as suffering from regional ileitis (Crohn's disease), viral thyroiditis, multiple-sclerosis, viral hapatitis, viral diverticulitis, carpal tunnel syndrome, psoriasis, amyotrophie lateral sclerosis, cytomegalovirus infection, viral macular degeneration of the retina and measles. Where the viral infection was suspected in view of a broad general deterioration, but specific diagnosis was inconclusive, the treatment often appeared effective in lengthening life and maintaining strength. In non-human mammals, the treatment is considered apparently effective in controlling such viral diseases as distemper and scrapie in sheep.

A typical intense treatment for an average size human adult patient comprises 500 mgs of the agent three to four times daily for a period of many months, then a reduction to 250 mgs three or four times daily for many additional weeks and thereafter further reduction or discontinuance, depending upon the tolerance of the patient and absence of symptoms. Doses for children and veterinary use are proportionally less according to body weight.

As a more specific example of treating a child, an eight year old white female developed a rash on her arms and legs; her eyes were watery and she complained of itching. She had not received a measles virus injection prior to the onset of the disease. When the patient was seen, she appeared to have contracted measles and exhibited a temperature of 102.8 degrees orally. She had a blotchy rash all over her body, with the characteristic measles cough. The patient was started on metronidazole, 125 mg t.i.d. with food and treated for one week. In less than 24 hr after starting treatment there was a dramatic change in the child's subjective and physical signs; she was markedly improved with just a low grade temperature, 99.2 degrees orally, and the rash was rapidly fading. To confirm the diagnosis, measles titers were taken two weeks apart, the first being less than one to eight; the latter being one to 32, which serologically is diagnostic for measles.

It is suggested that consideration should be given to treating measles as noted rather than the use of live virus injection, which has been associated with the possibility of causing diseases such as multiple-sclerosis. Also, if a reliable early detection of multiple-sclerosis can be developed, arrest and possible cure may be available through the disclosed treatment.

Another specific example concerned a forty-one year old white male who experienced marked fatique and weakness to the point that he was unable to work at his job as an elevator installer. He developed severe nausea and vomited for forty-eight hours. His urine became dark and he suffered marked abdominal pain. Positive diagnosis was infectious hepatitis. The patient was started on metronidazole 125 mgs t.i.d. with food and treated for about five months. Positive results were noticed in about five days after initiating treatment. He returned to full time work after about thirty-five days and there has been no recurrence for over five years.

An ultimate effective long-time maintenance dose was found to be as low as 31 mgs per day. The most common effective maintenance dose has been determined to be about 250 mgs per day for a substantial percentage of patients, with 500 mgs per day being indicated and well tolerated for other patients, depending on age, size, and physical condition. A reasonable maximum dosage for adult humans appears to be about 2,000 to 2,500 mgs per day. Renewal of treatment has been found to be effective upon a return of symptoms after treatment was discontinued.

Regarding side effects, some persons were found to experience nausea but it generally disappeared after a few weeks. In rare instances there was a slight soreness of the mouth or a white tongue indicating need for dosage reduction. Some dizziness and dryness of the mouth and vagina were occasionally noted and a few persons complained of a bad taste. Also, moderate leukopenia was occasionally observed, which normally returned to normal after dosage reduction, completion of a treatment regimen or as therapy continued.

Metronidazole is believed contraindicated in patients under treatment with desulfadram (Antabuse) and in hypothyroid patients. Because metronidazole appears to cross the placental barrier and enter the fetal circulation rapidly and further since its effect on fetal development are not definitely known, it is also thought to be contraindicated during the first trimester of pregnancy, except when a history of prior existing viral infection may endanger that pregnancy.

The initial neurological signs of metronidazole overdose in humans appear to be increased pulse rate, difficulty in reading small pring, difficulty in handling small objects and insomnia. Progressively, it is understood that tachycardia may occur, and a slightly unstable person, especially, may suffer marked swings in mood. Physical exercise apparently becomes increasingly fatiguing, and weight loss occurs to spite substantial food intake. When the medication is withdrawn, the adverse reaction usually clears in one week.

The metronidazole treatment described does not appear to damage the hematopoietic or the reticuloendothelial systems.

Over the past several years metronidazole has been tried with various effectiveness for the treatment of trichomonas vaginalis infections, alcoholism, ameobic dysentery, ameobic liver abcess, leishmaniasis and giardia infestations, acute ulcerative gingivitis, long standing indolent ischemic ulcers found in peripheral vascular disease, scleroderma, schizophrenia and in diabetic retinopathy, but apparently its effectiveness in viral infections has not been heretofore known.

Metronidazole apparently interferes directly with the synthesis of DNA viruses, in a similar manner that occurs with cytosine arabinoside. Metronidazole also apparently interferes with protein synthesis, as uric acid levels increase during therapy and may in some instances manifest itself in acute gout.

It is to be understood that while certain practices of this invention have been described herein, it is not to be limited to the specific form described except insofar as such limitations are inluded in the following claims.

What I claim and desire to secure by Letters Patent is:

1. A method for treating a human host having a viral hepatitis infection comprising:
   (a) repeatedly orally administering anti-hepatitis viral infection effective amounts of a pharmaceutical composition which contains, as an active ingredient, 1-(B-hydroxethyl)-2-methyl-5-nitromidazole to a human host in need of said treatment.
2. The methd of claim 1 wherein:
   (a) the dosage range of the composition in adult human patients is about 31 mgs to 2,500 mgs per 24 hour period.
3. The method of claim 1 wherein:
   (a) the dosage amount is substantially reduced following initial administration over a period including a plurality of months.
4. The method of claim 1 wherein:
   (a) said composition is administered at a dosage of about 250 mgs per 24 hour period.

* * * * *